United States Patent
Royall et al.

(10) Patent No.: US 6,255,510 B1
(45) Date of Patent: Jul. 3, 2001

(54) PRODUCTION OF AROMATIC CARBOXYLIC ACIDS AND RECOVERY OF CO/MN CATALYST FROM ASH

(75) Inventors: David John Royall, Cleveland; Julie Ann Bartlett, North Yorkshire; Roger Gaskell Fairhurst, Cleveland, all of (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/308,124
(22) PCT Filed: Nov. 12, 1997
(86) PCT No.: PCT/GB97/03099
§ 371 Date: Mar. 24, 2000
§ 102(e) Date: Mar. 24, 2000
(87) PCT Pub. No.: WO98/22216
PCT Pub. Date: May 28, 1998

Related U.S. Application Data
(60) Provisional application No. 60/032,598, filed on Dec. 2, 1996.

(30) Foreign Application Priority Data

Nov. 18, 1996 (GB) .................................... 9623897
Dec. 2, 1996 (GB) .................................... 9625033

(51) Int. Cl.⁷ ........................... C07F 13/00; C07F 15/02; B01J 20/34
(52) U.S. Cl. .............................. 556/49; 556/149; 502/24; 502/28
(58) Field of Search ........................ 502/24, 28; 556/49, 556/149

(56) References Cited

U.S. PATENT DOCUMENTS

| | | | |
|---|---|---|---|
| 4,876,386 | * 10/1989 | Holzhauer et al. | 562/414 |
| 5,840,643 | * 11/1998 | Park et al. | 502/25 |
| 6,001,763 | * 12/1999 | Feitler et al. | 502/27 |

* cited by examiner

*Primary Examiner*—Porfirio Nazario-Gonzalez
(74) *Attorney, Agent, or Firm*—Charles E. Krukiel

(57) ABSTRACT

Cobalt and/or manganese is recovered from the ash obtained following incineration of the catalyst containing residue arising from the liquid phase oxidation of an aromatic carboxylic acid such as terephthalic acid. Recovery is effected by contacting the ash with an organic acid or an organic acid anhydride such as acetic anhydride, optionally in the presence of bromide ions (e.g. HBr), so that the cobalt and/or manganese metals are recovered as monocarboxylic acid soluble salts thereof thus permitting recycle thereof to the liquid phase oxidation process.

2 Claims, No Drawings

PRODUCTION OF AROMATIC CARBOXYLIC ACIDS AND RECOVERY OF CO/MN CATALYST FROM ASH

This Appln is a 371 of PCT/GB97/03099 Nov. 12, 1997, which claims benefit of 60/032,598, filed Dec. 2, 1996.

This invention relates to the production of aromatic carboxylic acids such as terephthalic acid and isophthalic acid.

Terephthalic acid for example is produced commercially by oxidising p-xylene with oxygen in a liquid phase which comprises a lower aliphatic carboxylic acid solvent, such as acetic acid, and a dissolved heavy metal catalyst system (usually cobalt and manganese and a bromine promoter). A slurry of terephthalic acid in the solvent is withdrawn from the reactor and is subjected to a solids-liquid separation process resulting in crude terephthalic acid crystals which may be subsequently processed further and a mother liquor filtrate which, in addition to catalyst and promoter used in the oxidation reaction, contains dissolved terephthalic acid and various by-products and impurities. These by-products and impurities arise from various sources such as minor impurities in the p-xylene feed stock to the reaction, incomplete oxidation of p-xylene resulting in partially oxidised products and by-products arising from the competing side reactions in the oxidation of p-xylene to terephthalic acid.

It is common practice to recycle a large proportion of the recovered mother liquor to the oxidation reaction in order to return catalyst and promoter to the oxidation reaction while purging a smaller proportion to a solvent recovery system so as to maintain the level of impurities and by-products in the reaction within tolerable limits. In the solvent recovery system, the mother liquor purge is subjected to evaporation to remove a substantial proportion of the aliphatic acid solvent and water present (which can be returned to the oxidation reaction) leaving a concentrate containing terephthalic acid and impurities/by-products together with some of the heavy metal catalyst present in the original mother liquor filtrate. The concentrate (the residues) may then be disposed of or, if economically justifiable, treated in order to recover valuable components for recycling, e.g. catalyst metals. Typical downstream treatments of the residues include catalyst recovery, pyrolytic decomposition to eliminate substantially all of the organic content of the residues (e.g. by incineration in a high temperature furnace) and anaerobic/aerobic biological treatment to reduce chemical oxygen demand (COD).

The present invention is concerned with catalyst metal recovery via pyrolysis of the residues where the catalyst metals are present to a significant extent in their (III) and/or (IV) states as oxides thereof and as such are insoluble in water and only very sparingly soluble in acids.

U.S. Pat. No. 3,341,470 discloses incinerating the residues to oxide ash and dissolving the ash with sulphuric acid containing chloride. The manganese and cobalt components are recovered by treatment of the solution with sodium carbonate to precipitate cobalt and manganese as their carbonates. The recovered carbonates are then treated with acetic acid to produce acetates for recycle to the oxidation reaction.

U.S. Pat. No. 4,786,621 discloses recovery of cobalt and manganese, and other metals, in the form of their acetate salts directly from mixed metal oxides present in incinerator ash comprising fly ash and clinkers. The process recovers these metals by use of acetic acid at about the boiling point or reflux temperature and atmospheric pressure in conjunction with use of cobalt metal or hydrazine as reducing agent.

U.S. Pat. No. 4,546,202 discloses recovery of cobalt and manganese from solid aromatic acid incinerator ash by combining the ash with glacial acetic acid, or mixtures of acetic acid and water and heating the mixture under pressure in a stirred reactor. Although it is acknowledged that hydrobromic acid will react with cobalt and manganese oxides, the described reaction is conducted in the absence of bromide.

According to the present invention there is provided a process for the recovery of cobalt and/or manganese from ash containing cobalt and/or manganese as oxides thereof, comprising contacting the ash with an organic acid or an organic acid anhydride with or without bromide ions and recovering the cobalt and/or manganese.

Preferably the cobalt and/or manganese is recovered as acetic acid soluble salts thereof.

The invention is particularly applicable to the treatment of catalyst metal-containing residues obtained by treatment of the mother liquor purge in the course of the production of aromatic carboxylic acids by the liquid phase oxidation of a hydrocarbon precursor of the aromatic carboxylic acid in a monocarboxylic acid solvent containing a catalyst system comprising cobalt and/or manganese and a promoter such as bromine.

We have found that recovery of cobalt and/or manganese can be secured using acetic acid or acetic anhydride without introducing bromide ions to the recovery process; however, recovery can be significantly enhanced without employing high temperature and pressure conditions if bromide ions are present in the reaction.

The present invention is based on the recognition that dissolution of the otherwise difficult to dissolve cobalt and/or manganese oxides obtained following pyrolysis, e.g. incineration, can be readily achieved using an aliphatic acid or aliphatic acid anhydride such as acetic anhydride, preferably in conjunction with a bromide.

The bromide ions may be introduced initially so that the reaction between the anhydride and the ash takes place in the presence of bromide ions. Alternatively, the bromide ions may be introduced after the reaction between the acid or anhydride and the ash has been initiated. Conveniently the amount of bromide employed comprises from 0.5 to 2.0 moles (preferably less than 2 moles, between 0.5 and about 1.5 to 1.8 moles) of bromide for each mole of cobalt or manganese.

In practising the process of the invention, the amount of bromide employed need only be approximately the molar equivalent of the cobalt and/or manganese content of the ash. The use of an amount of bromide which is less than the molar equivalent of the cobalt and/or manganese content of the ash will result in lower recovery of the metals. However, this may be advantageous since operation in a bromide lean regime allows greater flexibility for adjustment of final bromide to metals ratio and may reduce or eliminate the need to treat bromine-containing offgas. Also, in this event, the cobalt/manganese containing residue remaining after treatment can be recycled for further treatment by the process of the invention.

Preferably the bromide is present in the form of hydrogen bromide although we do not exclude the possibility of using other bromides such as acetyl bromide. Thus, according to a preferred aspect of the invention approximately one mole of hydrogen bromide is employed for each mole of metal present in the ash. Thus, for example, where the ash contains both cobalt and manganese oxides, the hydrogen bromide employed corresponds to about one mole per mole of each metal. However, we do not exclude the possibility of greater amounts of bromide being used although, in this event, bromine evolution during the course of the reaction may give rise to increased problems in terms of treating and disposing of bromine-containing gases. Nevertheless as referred to below, greater amounts of bromide may be advantageous in terms of controlling the bromide to metals ratio of the catalyst/promoter system supplied to an oxidation reaction for the production of aromatic carboxylic acids.

Where bromide ions are employed, preferably the bromide is introduced in a liquid phase vehicle; for example dissolved in an aliphatic acid such as acetic acid, or in water.

The organic acid anhydride employed is conveniently acetic anhydride. The organic acid is conveniently acetic acid. A mixture of an organic acid and an organic acid anhydride may also be used and has been found to be effective. Preferably such a mixture should comprise an organic acid and the corresponding acid anhydride, for example a mixture of acetic acid and acetic anhydride is suitable for use in the reaction. If water is present in the reaction mixture with an organic anhydride, then the anhydride may be wholly or partially hydrolysed to the corresponding acid, the resulting mixture of the acid and the anhydride being used in the reaction.

The ash which contains the metal oxides may be wet. The ash may be recovered from a wet oxidation process or it may be produced in a dry state and then washed.

We have found that the presence of water above certain levels in the reaction may be detrimental to the recovery of the metals. The reaction is preferably carried out in dry conditions but some water may be tolerated without greatly reducing the recovery of cobalt or manganese. The water content of the reaction mixture is preferably less than 30% by weight and more preferably less than 20%, especially less than 15% by weight. Water may be present in the reaction mixture as a result of using wet ash or providing the hydrogen bromide as a solution in water, for example. When wet ash is introduced into the reaction with an organic anhydride present, some water may be removed from the reaction by reaction with the anhydride to form the corresponding acid . Therefore if wet ash is used and it is desired to operate the reaction under substantially dry conditions, the wet ash may be added to an organic anhydride, with which the water will react to form an organic acid. This hydrolysis reaction generates heat and thus the completion of the hydrolysis may be inferred from the cessation of heat generation, following which further anhydride or dry acid may be added to complete the reaction. If the amount of water in the ash is too high to be removed by the hydrolysis of anhydride, or if acid is used instead of anhydride such that the amount of water present is likely to be detrimental to the reaction then wet ash may be dried prior to its introduction into the reactor. The organic acid generated by the hydrolysis of the anhydride by water which is present in the reaction is preferably used in a different part of the process, e.g. it may be returned to an aromatic acid precursor oxidation reaction from which the ash has been generated. The amount of acid produced is dependent upon the amount of water in the catalyst recovery reaction mixture and therefore the amount of water allowed in the reaction mixture is preferably controlled so that the ratio of recovered catalyst to acid produced is suitable for direct recycle to the originating oxidation reaction.

U.S. Pat. No. 4,490,297 which discloses recovery of cobalt and manganese by precipitating cobalt and manganese directly from the oxidation mother liquor as oxalate dihydrate salts thereof followed by the conversion of the oxalate dihydrate salts into an acetic acid soluble form by reaction with acetyl bromide, hydrogen bromide or a mixture thereof in acetic acid or acetic anhydride. U.S. Pat. No. 4,490,297 is not concerned with the incineration of residues and does not therefore address the problem of recovering cobalt and/or manganese from oxides thereof in which the metals are in their (III) and/or (IV) states. U.S. Pat. No. 4,490,297 further teaches using 2 to 4, preferably 2 to 2.2, moles of hydrogen bromide and 3 to 4, preferably 3.1 to 3.5, moles of acetic anhydride per mole of the cobalt and/or manganese oxalate dihydrate.

Surprisingly we have found that, where bromide is used (especially when in the form of hydrogen bromide), even sub-stoichiometric levels of the bromide enhance recovery of the metals significantly and if the bromide is increased so that one mole of bromide is provided for each mole of metal in the ash, the recovery approaches 100% efficiency. Because the amount of bromide employed need only be limited to one mole per mole of cobalt and/or manganese, the bromide to total catalyst metals ratio in the recovered metals is suitable for direct recycle to the aromatic acid oxidation reaction.

Incineration may be carried out using any suitable technique for disposing of ash-forming liquids and/or solids by high temperature oxidation.

According to a more specific aspect of the present invention there is provided a process for the production of an aromatic carboxylic acid (such as terephthalic acid or isophthalic acid) in which:

a precursor of the aromatic acid is oxidised in a C2–C6 monocarboxylic acid solvent containing a catalyst system comprising cobalt and/or manganese compounds, a slurry comprising crystals of the aromatic acid in solvent-based mother liquor is withdrawn from the reaction zone and subjected to a solids-liquid separation, at least part of the mother liquor is treated to produce a residue containing cobalt and/or manganese, the residue is pyrolised to produce ash containing cobalt and/or manganese oxides, and cobalt and/or manganese is recovered as salts thereof soluble in said monocarboxylic acid by treatment with an organic acid or organic acid anhydride, preferably in the presence of bromide ions.

Where bromide ions are present, they may be present initially or they may be introduced after the reaction between the organic acid or anhydride and the ash has been initiated.

The recovered cobalt and/or manganese salts are preferably recycled to the oxidation zone.

Where bromide is used, a notable feature of this aspect of the invention is that the resulting bromide to metals ratio in the recovered material is compatible with recycle to the oxidation zone without the need for adjustment or further treatment to reduce the bromide ion concentration in the solution, as outlined in U.S. Pat. No. 4,490,297 because in the process of the present invention recovery may be essentially stoichiometric on bromide ion with one mole of either cobalt or manganese being extracted per mole of bromide.

In contrast, while hydrobromic acid has previously been referred to in U.S. Pat. No. 4,786,621 for use as a reducing agent in the recovery of cobalt and manganese recovery from the residue obtained in the production of trimellitic acid residue, the bromide to metals ratio is stated to be unacceptable. Similarly, in U.S. Pat. No. 4,298,580, the use of hydrobromic acid to precipitate cobalt and manganese as their bromides (requiring at least 2 moles hydrobromic acid per mole of metal) is not favoured because the bromide to metals ratio is too high.

The reason for the reduced amount of bromide required in practising the preferred embodiment of the invention appears to stem from the presence of the anhydride and the apparent formation of bromoacetate salts of the cobalt and/or manganese. In simplistic terms, the process is believed to involve reactions of the following form:

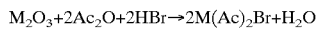
$$M_2O_3 + 2Ac_2O + 2HBr \rightarrow 2M(Ac)_2Br + H_2O$$

where M represents cobalt and/or manganese.

However, the reaction involved is undoubtedly more complex than this since flyash is a complex mixture of oxides in high oxidation states. A minor amount of the hydrobromic acid may be oxidised to bromine gas which is particularly corrosive and is an environmental hazard. We have found this compound to be substantially reduced by the addition of a small amount of hydrocarbon compound to the reaction. This hydrocarbon is conveniently the precursor for the oxidation process being operated; for instance p-xylene in the case of terephthalic acid production and m-xylene in the case of isophthalic acid production. However since the amount of hydrocarbon required for this purpose is relatively low, virtually any hydrocarbon would suffice. Other compounds which may be added to suppress the oxidation of the bromide to bromine include reducing agents such as formic acid, formaldehyde and acetaldehyde.

As indicated above, the resulting solution containing cobalt and/or manganese salts is particularly suitable for direct recycle to the oxidation zone. Where the oxidation process involves partial recycle of mother liquor containing catalyst components, loss of bromide ion promoter (mainly as volatile organo-bromides) tends to occur. This necessitates an increased amount of bromide ion being required in the make up catalyst to maintain the required bromide to total catalyst metals ratio in the oxidation reaction, the increased bromide being dependant on the amount of mother liquor recycled. The bromide to metals ratio of the resulting recovered solution is particularly amenable to adjustment to give the required ratio and therefore, where bromide ions are used in the catalyst recovery process of the present invention, in selecting the amount of bromide used in the recovery process, consideration may be given to the level of bromide needed for adjustment of the bromide content of the mother liquor recycle to the oxidation reaction, as well as taking into account the amounts of cobalt/manganese present in the residue to be treated. In this manner, the reduced level of bromide in the mother liquor recycle can be compensated for by appropriate selection of the amount of bromide used in the catalyst recovery process.

The organic acid or acid anhydride used in the recovery of the catalyst is preferably the same acid, or an anhydride derived from the same acid, as that used as a solvent for the aromatic acid in the oxidation reaction. In this way the recovered catalyst solution may be recycled directly to the oxidation reaction. The oxidation of the aromatic acid is normally carried out in an acetic acid solvent and therefore it is convenient to use acetic acid or acetic anhydride in the recovery of the catalyst.

Removal of any contaminant metals present in the residue, e.g. iron, copper and chromium, may be effected using the teaching of the prior art, for example see GB Patent Nos. 1413488 and 1319172 following the anhydride/bromide treatment of the present invention. Another option is to remove iron for example by ion exchange treatment.

The invention will now be illustrated by way of example only with reference to the following Examples.

EXAMPLE 1

Flyash (0.9985 g) containing approximately 33–36 wt % cobalt and 33–36% manganese was stirred and heated under reflux with acetic anhydride (25 ml), and 33% hydrogen bromide in glacial acetic acid (1.5 g, 0.0061 mole HBr) for 2 hours. The mixture was cooled then diluted with distilled water (50 ml) to decompose the excess anhydride. The resulting solution was filtered and made up to 100 ml with distilled water to give a pink solution. Analysis by atomic emission spectroscopy showed the solution contained 0.23% manganese and 0.236% cobalt, a total of 0.008 moles of metal, showing a total of 1.2 moles of metal being extracted in combination with 1 mole of bromide ion added initially. Total elemental bromine was analysed by X-ray Fluorescence at 0.384% hence the solution bromide to metals ratio was 0.82. The bromide result indicates a loss of 0.104 g. The residue weighed 0.2917 g.

EXAMPLE 2

Flyash (1.0002 g) containing approximately 33–36 wt % cobalt and 33–36% manganese was stirred and heated under reflux with acetic anhydride (25 ml), and 33% hydrogen bromide in glacial acetic acid (2.5 g, 0.0102 mole HBr) for 2 hours. The mixture was cooled then diluted with distilled water (50 ml) to decompose the excess anhydride. The resulting solution was filtered and made up to 100 ml with distilled water to give a pink solution. Analysis by atomic emission showed the solution contained 0.283% manganese and 0.298% cobalt, a total of 0.0102 moles of metal showing a total of 1 moles of metal being extracted in combination with 1 mole of Bromide ion added initially. Total elemental bromine was analysed by X-ray Fluorescence at 0.597% hence the solution bromide to metals ratio was 1.03. The bromide result indicates a loss of 0.219 g. The residue weighed 0.1113 g.

EXAMPLE 3

Flyash (25 g) containing approximately 33–36 wt % cobalt and 33–36% manganese was stirred with acetic anhydride (250 ml) and 33% hydrogen bromide in glacial acetic acid (75 g, 0.3056 mole HBr) and then heated under reflux for 2 hours. Bromine gas was liberated as the heating started. The mixture was cooled then diluted with distilled water (100 ml) to decompose the excess anhydride. The resulting solution was filtered and made up to 500 ml with distilled water to give a pink solution. Analysis by atomic emission showed the solution contained 1.49% manganese and 1.53% cobalt, a total of 0.265 moles of metal, showing a total of 0.87 moles of metal were extracted in combination with one mole of bromide ion added initially. Total bromine was analysed by X-ray Fluorescence at 4.6% (0.288 moles total) hence the resulting bromide to metals ratio was 1.52. The bromine analysis indicates a loss of 7%. The residue weighed 1.1 g and contained 16.56% cobalt and 16.33% manganese. Hence recovery of both cobalt and manganese into solution was in excess of 97.5%.

EXAMPLE 4

Flyash (10 g) containing approximately 33–36 wt % cobalt and 33–36% manganese was stirred with acetic anhydride (90 ml), 33% hydrogen bromide in glacial acetic acid (30 g, 0.122 mole HBr) and p-xylene(10 ml) to suppress bromine evolution, and then heated under reflux for 2 hours. No bromine gas was observed to be liberated. The mixture was cooled then diluted with distilled water (70 ml) to decompose the excess anhydride. The resulting solution was filtered and the organic layer separated off and the aqueous layer made up to made up to 500 ml with distilled water to give a pink solution. The organic layer was analysed by combined gas chromatography and mass spectroscopy and shown to be largely a mixture of p-xylene, p-xylyl bromide, methylbenzyl acetate, and 4'4-dimethylbibenzyl all of which are terephthalic acid precursors. The pink aqueous solution was analysed by atomic emission and shown to contain 0.604% manganese and 0.618% cobalt, a total of 0.107 moles of metal, showing a total of 0.88 moles of metal were extracted in combination with one mole of bromide ion added initially.

EXAMPLE 5

Flyash (5 g) containing approximately 33–36 wt % cobalt and 33–36% manganese was stirred and heated under nitrogen at autogeneous pressure at 200° C. with acetic anhydride (40 ml) for 2 hours. The pressure rose to 75 psi. On cooling to ambient temperature the mixture was diluted with distilled water (50 ml) to decompose the excess anhydride. The resulting solution was filtered and made up to 200 ml with distilled water to give a brown solution. Analysis by atomic emission showed the solution contained 0.46% manganese and 0.45% cobalt, a recovery of 50% of the metal in the initial charge. The residue weighed 2.4 g

EXAMPLE 6

1 g (approximate) quantities of flyash comprising 39.3% Mn and 38.4% Co (as measured by inductively coupled plasma/atomic emission spectroscopy (ICP/AES) were reacted with acetic acid, water and HBr in appropriate quantities to give the various stated percentages of water shown in Table 1 and a metals:bromide ratio of 1:1.

The mixtures were stirred and refluxed for 2 hours and all were observed to turn dark green and evolve bromine gas. The mixtures were cooled overnight and 50 mls of distilled water added to each. After filtration, the filtrates were made up to 100 mls with distilled water before analysis by ICP/AES to give the results shown in Table 1.

The results indicate that the presence of water in the reaction mixture reduces the recovery of both cobalt and manganese.

EXAMPLE 7

25 g of flyash (39.3% Mn, 38.35% Co) were mixed with 250 mls glacial acetic acid and 60.5 mls of 33% HBr in acetic acid (to give total metals:bromide ratio of 1:1). Evolution of a small amount of bromine gas was observed. The mixture was then heated under reflux for 2 hours, more bromine gas was evolved. The mixture was then cooled, allowed to stand, and then added to about 500 mls of distilled water and filtered. The residue was dried at room temperature & weighed (1.9 g). The filtrate was made up to 1000 mls with distilled water and analysed by ICP/AES and the recovery of metals in the solution was calculated as 78% Mn and 76% Co. The solution was also analysed by X-ray fluorescence and found to contain 2.03% by weight of bromine.

TABLE 1

| water content % | Mn recovery % | Co recovery % |
|---|---|---|
| 0 | 81.6 | 82.3 |
| 4.4 | 80 | 73.6 |
| 14.4 | 71.3 | 70 |
| 19.4 | 59 | 57.2 |
| 23.4 | 57.9 | 56.4 |

TABLE 1-continued

| water content % | Mn recovery % | Co recovery % |
|---|---|---|
| 28.1 | 56.9 | 55.6 |
| 51.9 | 41.8 | 43 |

EXAMPLE 8

1.3797 g of the dry residue from Example 7 were then extracted again, using 25 mls of glacial acetic acid and 3.34 mls of 33% HBr in acetic acid, to give total metals:bromide ratio of 1:1, based on an estimated quantity of metals in the residue. The mixture was refluxed for 2 hours, cooled, allowed to stand overnight, and then added to 50 mls of distilled water. After filtration, the filtrate was made up to 100 mls with distilled water. Analysis by ICP/AES gave a recovery of metals (based on the estimate of metals in the residue) of 23% Mn and 86% Co. The total bromine in the solution, measured by X-ray fluorescence, was 1.23% w/w. This result shows that the residue from a first metals extraction may be successfully recycled to a second extraction process to yield a further quantity of recovered metals.

EXAMPLES 9–14

A series of synthetic "flyash" compounds were made to provide samples having Mn:Co ratios of approximately 2:1, 1:1 and 1:2 w/w. These samples were prepared by ashing residues from a p-xylene oxidation plant of known metals content at 550° C. overnight and then adding a calculated amount of cobalt acetate solution to produce the desired ratio of cobalt to manganese before re-ashing the samples and determining the weight of Mn and Co by ICP/AES.

One sample of each synthetic flyash was washed with distilled water to remove sodium and then dried. The washed and the unwashed samples were extracted according to the following procedure. Approximately 1 g of each flyash was accurately weighed and mixed with 25 mls of acetic acid and a volume of 33% HBr in acetic acid to give a total metals:bromide ratio of 1:1. The mixtures were refluxed for 2 hours and evolution of bromine gas was observed. The mixtures were cooled overnight, and added to 50 mls of distilled water. After filtration, the filtrates were made up to 100 mls with distilled water and the residues were dried at room temperature.

The solutions were analysed for metals by ICP/AES and for bromine by X-ray fluorescence. The results are shown in Table 2.

TABLE 2

| Example no. | weight Mn:Co | washed | recovery Mn % wt | recovery Co % wt | wt % bromine in solution |
|---|---|---|---|---|---|
| 1 | 2.2:1 | No | 65 | 75 | 0.29 |
| 2 | 1.1:1 | No | 63 | 71 | 0.43 |
| 3 | 1:2.2 | No | 73 | 55 | 0.37 |
| 4 | 2.2:1 | Yes | 68 | 79 | 0.29 |
| 5 | 1.1:1 | Yes | 58 | 67 | 0.31 |
| 6 | 1:2.2 | Yes | 72 | 54 | 0.34 |

EXAMPLES 15–19

Approximately 1 g quantities of flyash (containing 39.3% Mn and 38.4% Co as measured by ICP/AES) were reacted with 25 ml of glacial acetic acid and measured quantities of 33% HBr in acetic acid to give various different metals:bromide ratios. In each case the reagents were simply mixed and allowed to stand for approximately 18 hours and then added to 50 ml of distilled water. The resulting mixtures were then filtered and the filtrates made up to 100 ml with distilled water and then analysed by ICP/AES. The metals:bromide ratios and the resulting metals recoveries are shown in Table 3.

TABLE 3

| Example | total metals:bromide | Mn recovery w % | Co recovery w % |
| --- | --- | --- | --- |
| 15 | 1:1 | 41.7 | 44.1 |
| 16 | 2:1 | 28 | 28.7 |
| 17 | 4:1 | 16.5 | 18.2 |
| 18 | 8:1 | 11.4 | 11.7 |
| 19 | 1:2 | 53.4 | 54.7 |

The results show that a significant proportion of the metals may be recovered using a room temperature process, although the recovery is enhanced by heating the reagents to reflux temperature. Also an increased proportion of bromide to metals increased the recovery of metals but the recovery was possible over a wide range of metals:bromide ratios.

What is claimed is:

1. A process for the recovery of cobalt and/or manganese from fly ash containing cobalt and/or manganese as oxides thereof which comprises contacting the fly ash with an organic acid anhydride, an organic acid or a mixture thereof in the presence of from 0.5 to 2.0 moles of bromide per mole of cobalt plus manganese in a reaction mixture which contains less than 30% by weight water and at a temperature in the range of from ambient temperature to reflux temperature and recovering the cobalt and/or manganese as soluble salts.

2. The process of claim 1 in which the organic acid anhydride is acetic anhydride, the organic acid is acetic acid, and the bromide is introduce into the reaction in the form of hydrogen bromide or acetyl bromide.

* * * * *